(12) United States Patent
Portela Da Gama et al.

(10) Patent No.: US 9,205,103 B2
(45) Date of Patent: Dec. 8, 2015

(54) DEXTRIN HYDROGEL FOR BIOMEDICAL APPLICATIONS

(75) Inventors: Francisco Miguel Portela Da Gama, Oporto (PT); Maria Cabral Maio Molinos, Caminha (PT)

(73) Assignee: UNIVERSIDADE DO MINHO, Braga (PT)

( * ) Notice: Subject to any disclaimer, the term of this patent is extended or adjusted under 35 U.S.C. 154(b) by 531 days.

(21) Appl. No.: 13/515,228

(22) PCT Filed: Dec. 9, 2010

(86) PCT No.: PCT/IB2010/055695
§ 371 (c)(1),
(2), (4) Date: Sep. 18, 2012

(87) PCT Pub. No.: WO2011/070529
PCT Pub. Date: Jun. 16, 2011

(65) Prior Publication Data
US 2013/0045242 A1 Feb. 21, 2013

(30) Foreign Application Priority Data

Dec. 10, 2009 (PT) ........................................ 104879

(51) Int. Cl.
| | |
|---|---|
| *A61K 9/00* | (2006.01) |
| *A61K 31/721* | (2006.01) |
| *A61L 27/20* | (2006.01) |
| *A61L 27/22* | (2006.01) |
| *A61L 27/24* | (2006.01) |
| *A61L 27/38* | (2006.01) |
| *A61L 27/48* | (2006.01) |
| *A61L 27/52* | (2006.01) |
| *A61L 27/54* | (2006.01) |
| *A61L 27/56* | (2006.01) |
| *A61K 51/12* | (2006.01) |
| *A61K 47/36* | (2006.01) |

(52) U.S. Cl.
CPC ............... *A61K 31/721* (2013.01); *A61L 27/20* (2013.01); *A61L 27/227* (2013.01); *A61L 27/24* (2013.01); *A61L 27/38* (2013.01); *A61L 27/48* (2013.01); *A61L 27/52* (2013.01); *A61L 27/54* (2013.01); *A61L 27/56* (2013.01); *A61K 47/36* (2013.01); *A61K 51/1213* (2013.01); *A61L 2300/252* (2013.01); *A61L 2300/602* (2013.01); *A61L 2300/624* (2013.01); *A61L 2400/06* (2013.01); *A61L 2430/02* (2013.01)

(58) Field of Classification Search
None
See application file for complete search history.

(56) References Cited

U.S. PATENT DOCUMENTS

| | | | | |
|---|---|---|---|---|
| 5,624,668 | A | * | 4/1997 | Lawrence et al. .......... 424/78.17 |
| 2008/0069894 | A1 | * | 3/2008 | Royer .......................... 424/549 |

FOREIGN PATENT DOCUMENTS

| | | |
|---|---|---|
| WO | WO 98/12228 | 3/1998 |
| WO | WO 00/21572 | 4/2000 |
| WO | WO 2005/042048 | 5/2005 |
| WO | WO 2007034495 A2 * | 3/2007 |

OTHER PUBLICATIONS

International Search Report for International Application No. PCT/IB2010/055695 mailed Aug. 18, 2011.

* cited by examiner

*Primary Examiner* — James Rogers
(74) *Attorney, Agent, or Firm* — Merchant & Gould P.C.

(57) ABSTRACT

A hydrogel formulation of oxidized dextrin is reticulated with adipic acid dihydrazide, which may embody polysaccharides, proteins, nanogels, granular materials, bioactive molecules and cells for tissue regeneration and controlled drug delivery. A hydrogel can be injectable, highly biocompatible and biodegradable, for tissue regenerative applications, performing simultaneously as a vehicle e.g. for nanogels, granular materials and cells, and as controlled drug delivery systems, e.g. of hydrophobic molecules and therapeutic proteins.

29 Claims, 5 Drawing Sheets

DEXTRIN HYDROGEL FOR BIOMEDICAL APPLICATIONS

This application is a National Stage Application of PCT/IB2010/055695, filed 9 Dec. 2009, which claims benefit of Ser. No. 104879, filed 10 Dec. 2009 in Portugal and which applications are incorporated herein by reference. To the extent appropriate, a claim of priority is made to each of the above disclosed applications.

FIELD OF THE INVENTION

The present invention fits in the field of biomaterials with application in tissue regeneration, specifically focusing on the production of novel hydrogels of oxidized dextrin, which can be injectable, and with potential for inclusion and transportation of biomolecules, drugs, dextrin nanogels, and granular compounds, as well as for cell encapsulation.

BACKGROUND OF THE INVENTION

The increase in average life expectancy implies an overload in tissues and organs demand. In the last few years a great variety of hydrogels—class of three-dimensional, highly hydrated polymeric networks (water content ≥30% of total weigh)—has been developed and applied in tissue regeneration. These materials are composed of hydrophilic polymer chains, which can be either synthetic or natural, appealing for tissue engineering strategies due to the possibility of reproducibly mimetizing the chemical structure of biological tissues and its properties in general.

Synthetic and natural polymers have been explored as drug carriers. Unfortunately, the majority of the polymers used clinically, although well tolerated, are still non-biodegradable synthetic polymers e.g. poly(ethyleneglycol) (PEG) (Fuertges and Abuchowski, 1990) and N-(2-hydroxypropyl)methacrylamide (HPMA) copolymers, (Vasey et al., 1999). Thus in order to ensure renal elimination and to exclude the threat of progressive accumulation after repeated administration, only polymers with a molecular weight below the renal threshold (approximately 40,000 Da) can be used (Hreczuk-hirst et al., 2001).

A variety of natural materials may be used to form hydrogels for tissue engineering, such as collagen, chitosan, alginate and hyaluronic acid (HA). However, the performance of these materials in vivo is not always the best, as stated by Drury and Mooney (2003). Highly pure and homogeneous chitosan is quite difficult to produce; on the other hand, the pro-inflammatory bioactivity limits its biomedical usage. The safety of collagen materials is a concern, due to the risk of contamination. Alginate is also several times highlighted as a promising polysaccharide for hydrogels synthesis for tissue engineering applications. However, alginate is not specifically degraded, undergoing a slow uncontrolled dissolution, therefore being difficulty cleared of the body. Additionally, polymers like pullulan (Nogusa et al., 1995) or dextran (Nishikawa et al., 1996), also referred in this area, being inherently biodegradable, even with low levels of functionalization (to promote a drug linkage or to decrease degradation rates) can easily become non-degradable (Vercauteren et al., 1996). Some of these naturally derived polymers (including dextran) are immunogenic, impeding its repeated administration (Hreczuk-hirst et al., 2001). A Phase I study involving dextran-doxorubicin has shown evidences of hepatotoxicity (Danauser-Reidl et al., 1993).

Injectability is commonly a target property when developing hydrogels, assuring its administration in a minimally invasive procedure. Crosslinking time is a very important feature of these materials, determining its suitability to a specific application. For instance, a gelling period greater than 30 min is not adequate to a maxillofacial intervention.

The present invention, aiming to surpass the setbacks mentioned above, describes an injectable dextrin-based hydrogel, with potential for inclusion and transportation of biomolecules, drugs, nanogels, and granular compounds, as well as for cell encapsulation. Simultaneously, this biomaterial is intended to provide controllable crosslinking times and mechanical properties, through the adjustment of specific parameters, such as the degree of oxidation and concentration of the crosslinking agent. Dextrin means a glucose polymer produced by hydrolysis of starch, consisting of glucose units linked mainly by α-1,4 linkages. In addition to α-1,4, there may be a proportion of α-1,6 linkages, the amount depending on the source of the starch. Any dextrin is a mixture of glucose polymers of different chain lengths.

Dextrin-based hydrogel formulations are referred in a small number of articles and patents, reviewed ahead. Indeed, dextrin is an emergent tool in the biomedical field for its non-toxicity and non-immunogenicity (Treetharnmathurot et al., 2009). It has been FDA approved as the peritoneal dialysis solution Icodextrin™. Icodextrin (a polydisperse dextrin) has also been developed as carrier solution for intraperitoneal administration of an anticarcinogenic agent (Kerr et al., 1996). Recent work also reported the ability of dextrin conjugates to exhibit anti-endotoxin activity as well as to regulate the inflammatory response (Davtyan et al., 2007; Avetisyan et al., 2006). In another recent work, dextrin-hydroxyapatite (HAp) complex was used as a bone filling material, with good performance (Asai et al., 2009). In addition, a nanogel, organized by self-assembling of amphiphilic dextrin has been described as potential drug carriers (Gonçalves et al., 2007). A similar material—a dextrin nanogel—has been developed also by Orienti et al. (2009; WO2009/016663A1). Dextrin-based microspheres were used for encapsulation of the photosensitizer porphyrin, which aggregates in aqueous solutions, allowing its administration in the monomeric form, in photodynamic therapy (Luz et al., 2008). Colin Brown (2010) developed also a dextrin formulation capable of preventing or reducing the incidence on postoperative adhesions (US2010/0240607A1).

Recently, Carvalho et al. (2007) produced dextrin hydrogels, namely dextrin-VA and dextrin-HEMA, as controlled drug delivery systems. However, the method used to produce these hydrogels, i.e. radical polymerization, requires chemical initiators to activate the gelification process (e.g. ammonium persulfate), which might react with cellular structures and reveal toxic. In addition, it implies the modification of the dextrin main chain with acrylic monomers, and the gelification is fast. Hence, these dextrin-based materials do not possess the main required properties for an injectable hydrogel, essentially due to limitations such as cytotoxicity and lack of control over crosslinking times.

The proven clinical tolerability of dextrin, readily degraded by amylases (Davies, 1994), suggests it might gather excellent properties for the development of drug carrier systems and overall in biomedical applications. For this purpose it is particularly relevant the fact that dextrin is an abundant resource, being already available in a medical-grade formulation with excellent biocompatibility. Additionally, long plasma circulation times (hours or days) has been achieved by functionalization of the main polymeric chain, allowing an improved ability for tissue targeting (Hreczuk-hirst et al., 2001; Hardwicke et al., 2008; Treetharnmathurot et al., 2009). Dextrin's low molecular weight is also a crucial and determinant property, once it favors a healthy renal clearance.

The U.S. Pat. No. 5,541,234, by Unger et al., describes hydrogels with high porosity and low density, made of alginate and/or other polysaccharides, including dextrin, in which the polymer concentration originating the ideal density for the porous structure lies preferably between 1% and 10%. In the particular cases of agar, carrageenan, gelatins and caseins the crosslinking process takes place preferably at high temperatures, turning in situ gelation unfeasible, otherwise tissues surrounding the hydrogel could be seriously damaged. It is also stated the use of solvents along the crosslinking reaction, which, bearing in mind biomedical applications, is a clear disadvantage compared to the process described in the present invention. Unger et al. do not ply the possibility of associating biomolecules or cells. Moreover, the gelification relies strictly on the use of crosslinking agents, without previous modification of the polysaccharides. Dextrin, a glucose polymer, needs a pretreatment, e.g., oxidation by periodic acid, as proposed in this invention, allowing for the posterior gelification by the addition of a reticulating agent. Furthermore, still in the scope of the present invention, the polymer concentration that guarantees the ideal texture is 30%, giving rise to an injectable hydrogel, with appealing crosslinking times (5-30 min), which allows its unhurried handling and implantation, when used in maxillofacial surgery applications, as an adjuvant to osteogenic granular compounds. A polymer concentration bellow 25% will originate a viscous fluid instead of an hydrogel.

Bouhadir et al. (1999; US2007/07186413) conceived hydrogels for the controlled release of pharmaceuticals, based on the use of polysaccharides crosslinked with adipic acid dihydrazide (ADH), as in the present invention. The preferred polysaccharide is alginate. The procedure leading to the production of a hydrogel includes the partial oxidation of alginate followed by polymerization with ADH. This way, through oxidation of the polysaccharide, the authors aim the production of a material degradable in vivo. Indeed, the non-degradability is a main limitation to the biomedical use of alginates, since it avoids its efficient elimination and excretion. A better control over the gelification reaction is also envisaged, since the ionotropic gelification commonly carried out with alginate is unsatisfactory. In still another aspect of the patent, drug-polymer conjugates are developed, allowing an improved control of the drug release, in this case not based just on mass transfer phenomena.

In the case of the present invention, the retention of the biomaterial in the kidneys is not an issue, due to the low molecular weight of dextrin, whose degradation and removal may be controlled through the degree of substitution. In this regard, dextrin brings a clear advantage with when compared to alginates. On the other hand, in the present invention a strategy to avoid the quick release of pharmaceuticals from the highly porous hydrogel is purposed. Indeed, an additional degree of control on drug release may be achieved using nanogels with hydrophobic cores, able to solubilize poorly water-soluble pharmaceuticals, simultaneously allowing an additional control over the pharmacokinetic properties of the system. This is a rather simpler approach than the strategy purposed by Bouhadir and colleagues, based on the use of pharmaceutical-polymer conjugates. Additionally, these authors do not provide information on the profile of degradation of the hydrogels in physiologic medium, nor regarding its porosity, crucial parameters concerning its viability as drug controlled release systems. Furthermore, the alginate hydrogels reveal comparatively poor mechanical properties. For the same concentration of crosslinking agent (ADH), the resistance of the hydrogel to compressive forces (proportional to the number of intermolecular bonds) is lower for the alginate hydrogel, which is likely to translate also a poorer biodegradation profile.

In the U.S. Pat. No. 6,991,652 B2, Burg and colleagues describe composites made of a porous matrix of microparticles with variable geometry (spheres, cylinders or a net), preferentially made of collagen, which may be carried in a liquid or viscous fluid. In this invention, the composites are cultivated with cells, which may proliferate and originate a neo-tissue. Furthermore, the composites may be administrated by injection, in a minimally invasive manner, being claimed to be useful for a wide range of tissue engineering applications. Dextrin is referred as one of the materials which may constitute the fluid phase which carries the porous matrix, however the patent does not describe how hydrogels may be obtained from dextrin, whose function seems to be to increase the viscosity of the fluid phase. In the present invention, dextrin hydrogels may be associated e.g. to bioactive granules, ceramic particles, biomolecules or cells, as in the invention by Burg et al., and also with nanogels, namely dextrin nanogels, endowing the composite material with improved versatility, namely allowing its use for the transport and controlled release of bioactive molecules. Furthermore, this invention includes a methodology for the gelification of dextrin, which results in controllable mechanical properties and biodegradability, favoring its use for the controlled release of pharmaceuticals associated with the transport of a solid phase in an injectable system.

The patent WO2005/042048A2, from Hill et al., published in 2005, describes the production of injectable hydrogels made of proteins and polysaccharides, with gelification times of about 2 hours, allowing the incorporation of pharmaceuticals, namely, but not only, for bone regeneration. The concept developed for the gelification strategy is in this case based on the reactivity of the amine groups of the proteins and the polysaccharides. In the case of neutral polysaccharides the oxidation must be carried out first. This way, a lengthy gelification process results, as opposed to the obtained in the case of the present invention through the use of ADH.

The Japanese patent JP2005/298644A2, developed by Akiyoshi and colleagues, describe the production of a hybrid hydrogel, made of pullulan. The hydrogel is obtained by radical polymerization, using a mixture of methacryloil-pullulan with a nanogel of pullulan, also methacrylated. The nanogel self-assembles through hydrophobic interaction of cholesterol moieties grafted on the polysaccharide. This way, a hydrogel with a dispersed nanogel able to carry biopharmaceuticals, namely proteins, is obtained. The present invention also contemplates the incorporation of a nanogel as a drug controlled release device, differing from the Akiyoshi invention in relevant aspects, namely the high molecular weight of the pullulan used by Akiyoshi et al. (100 kDa) (as opposed to the low molecular weight dextrin) and the use of a polymerization initiator, 2,2'-Azobis [2-(2-imidazoline-2-yl) propane. While the patent does not describe details regarding the injectability of the hydrogel, the high molecular weight of pullulan raises doubts concerning the efficiency of the biological excretion, even more because it is not clear whether the intermolecular bonds are degradable. As a matter of fact, as it has been reported for methacryloil-dextran hydrogels, it is likely that methacryloil-pullulan hydrogels are not degradable in vivo (Cadée et al., 2000). On the other hand, the initiator may be toxic (Ameer et al., 2001). Thus, the use of the dextrin hydrogel, as well as of the dextrin nanogel, associated with the gelification method based on oxidized dextrin and ADH as reticulating agent, offer significant advantages, regarding biocompatibility and excretability. Later, Akiyoshi et al. (JP2009/149526A2) reported the use of the same hydrogel for the controlled release of cytokines.

The present invention is unique as it introduces a hydrogel made of dextrin, a hydrogel obtained through chemically simple and inexpensive methods, without using toxic initiators or catalysts. These processes originates a convenient speed of gelification as for handling the material, allowing its injectability into e.g. a tissue defect, for regeneration purposes, allowing the production of hydrogels with suitable mechanical properties and biodegradability for each application. These characteristics make possible the easy incorporation e.g. of biomolecules, bioactive ceramics and cells, as well as of nanogels (for instance of dextrin), resulting, in the late case, in a multidimensional composite (with a hydrophobic phase dispersed at the nano level), with improved versatility in the perspective of its use as a carrier for the controlled release of bioactive molecules.

The present invention relates to the production of hydrogels made of dextrin and adipic acid dihydrazide, which can be injectable, with application as 1) scaffold for tissue regeneration; 2) as a carrier of bioactive microspheres, e.g. bioactive osteogenic granular compounds for bone regeneration adjuvancy; 3) cell encapsulation; 4) vehicle for bioactive molecules (namely proteins or polysaccharides, e.g. collagen) which promote cell adhesion and proliferation, and 5) self assembled nanogels (e.g. made of dextrin) associated drug delivery systems.

In this invention, an expeditious methodology is used to prepare degradable hydrogels from oxidized dextrin (oDex) and adipic acid dihydrazide, without the use of any chemical initiator. Gelation periods from 1 to 30 minutes can be obtained, depending on the components concentration.

Dextrin homopolysaccharide chain can be oxidized using periodic acid. The periodate ion attacks one of the hydroxyl groups of the vicinal diol in dextrin residues, between C2-C3 positions of the glucopyranoside ring, breaking the C—C bond and yielding two reactive aldehyde groups. Aldehydes react with molecules such as adipic acid (ADH), which in turn acts as a reticulating agent, giving rise to hydrogels. The concentration of crosslinker directly affects the density of intermolecular bonds, which in turn influences the mechanical, degradation ang gelling properties of hydrogels. However, the amount of ADH used must be optimized taking into account the number of available oxidized residues, so that the number of viable chemical bonds is maximized, in detriment of the occurrence of pendant groups. Furthermore, the presence of excessive reactive groups may compromise the mechanical properties of hydrogels by effects of steric hindrance, for which the degree of functionalization of the polymeric chain must be moderate.

oDex/ADH hydrogels are degradable both hydrolytically, at the level of its covalent intermolecular bonds, and enzymatically, through the action α-amylase. Depending on the crosslinking density it is possible to obtain different degradation profiles. The tight structure of highly interconnected hundred nanometer pores becomes gently loose along the degradation process, allowing to predict some compliance towards cell invasion, once the material is injected, specially if the matrix exhibits chemoattractant signals or adhesion peptides, which may be easily introduced (for instance using nanogels loaded with bioactive molecules).

In terms of biocompatibility, dextrin hydrogels are non-toxic. Cells adhere and proliferate along its interface, allowing the perspectivation of a good tissue-hydrogel interaction in vivo. Additionally, oDex/ADH hydrogels are non-haemolytic.

Many advantages can be highlighted regarding oDex/ADH hydrogels in comparison with other known hydrogels, namely 1) simple and expeditious methodology of production; 2) absence of chemical initiators (generally toxic); 3) low molecular weight-favoring biodegradation and renal clearance; 4) biocompatibility; 5) possibility of inclusion/encapsulation of specific molecules/cells; 6) low-cost, naturally derived raw material, and already available in medical grade; 7) potential to perform as a carrier of microparticulate systems, for instance for bone regeneration applications; 8) great potential to perform as a controlled drug release system, both for biopharmaceuticals (therapeutic proteins) or water-insoluble molecules (through incorporation of nanogels with hydrophobic cores).

SUMMARY OF THE INVENTION

The present invention was made in view of the prior art described above and the object of the present invention is hydrogel formulations of oxidized dextrin reticulated with adipic acid dihydrazide comprising the following structure:

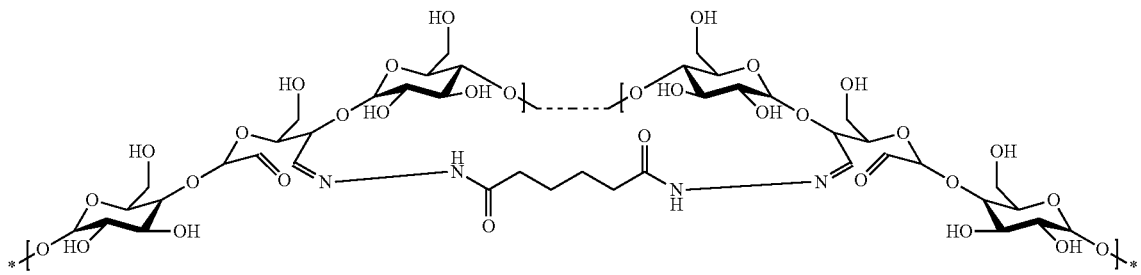

which possess the capacity of embodiment within its three-dimensional porous structure.

In a preferred embodiment the hydrogel embodies polysaccharides such as chitosan, hyaluronic acid, among others; proteins, such as collagen, fibronectin, casein, among others; nanogels; granular materials; bioactive molecules and cells.

In another preferred embodiment, proteins are included in a percentage between 0-20 of the hydrogel composition, dry weight, and polysaccharides are included in a percentage between 0-20 of the hydrogel composition, dry weight.

The hydrogel of the present invention is injectable, non-toxic and non-haemolytic.

In another embodiment the hydrogel is obtained from a dextrin with a oxidation degree between 10-50%, preferably between 25-35%, with a low molecular weight, between 1200-8000 Da and possesses a continuous porous structure, with a diameter of about 1 μm.

Further, in another embodiment, the biodegradation of the hydrogel occur by either surface or bulk erosion and is characterized by a non-linear degradation profile accompanied by an increase on pore size.

In another preferred embodiment the degradation of the hydrogel occur hydrolytically, at the level of its covalent intermolecular bonds, or enzymatically, through the action α-amylase present in human tissues or included in the hydrogel formulation.

Another object of the present invention is the producing method of the hydrogel formulation, which comprises the following steps:

a) oxidation of dextrin with periodic acid;
b) remotion of the unreacted periodate;
c) gelification from 1 to 30 minutes, by addition of a reticulating agent, such as adipic acid dihydrazide, preferentially at pH in the range 5.0-7.5, and at a concentration between 3-40%, preferably between 3-10%, on a molar basis relative to the glucose residues.

In a preferred embodiment the concentration of oxidized dextrin is between 5-40% (w/v), preferably between 25-30% (w/v).

In another preferred embodiment a nanogel is incorporated in the hydrogel in a proportion of 1-25% of the dextrin weight, by mixing the nanogel with the oxidized dextrin, previous to the addition of ADH, being the dimensions of the nanogel between 10-10000 nm.

In another preferred embodiment the nanogel is previously loaded with pharmaceuticals.

Another object of the present invention is the use of the hydrogel for tissue regeneration and controlled drug delivery.

Another object of the present invention is a biomaterial comprising the hydrogel.

Furthermore the present invention relates to a synthetic bone substitute comprising the hydrogel.

Another object of the present invention is a system for controlled drug delivery comprising the hydrogel.

Another object of the present invention is a bone implant or bone filler which comprises the hydrogel.

Furthermore the present invention relates to a composition which comprises an hydrogel.

Finally the present invention relates to a medical prosthesis which comprises the hydrogel of the present invention.

DETAILED DESCRIPTION OF THE INVENTION

Figure 1:
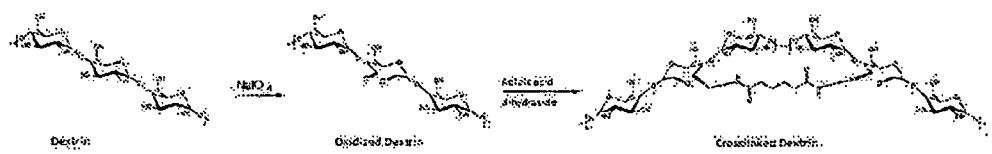
FIG. 1—Periodate oxidation of dextrin, yielding two aldehyde groups at positions C2 and C3 of a D-glucose unit.

Biomaterials are present in a growing number of clinical applications, being a central tool in new technologies such as tissue engineering, targeted delivery of pharmaceuticals, regenerative medicine, etc. The biocompatibility of biomaterials is a main requisite. Ideally, among other properties, a biomaterial should be non-toxic, non-immunogenic, have a favorable interaction with cells and tissues, in light of the envisaged application. For several applications, such as tissue engineering and drug delivery, biodegradability and full elimination/excretion are highly desirable. Dextrin, although quite abundant, inexpensive and available in medical grade, has been considered so far as a promising material but by a restricted number of scientists. Indeed, though, it seems to gather excellent biocompatibility, noteworthy the efficient elimination by the biological systems, due to its low molecular weight and biodegradation by amylases. This invention describes a hydrogel made of dextrin with interesting properties for biomedical applications which include, but not only, the delivery of pharmaceuticals and tissue regeneration. The simple fact that the hydrogel is made of dextrin represents a significant advantage.

This invention relates to a novel formulation of hydrogels made of oxidized dextrin reticulated with adipic acid dihydrazide, which possess the capacity of enclosing within its three-dimensional porous structure polysaccharydes, proteins, nanogels, microparticles or cells, for tissue regeneration and bioactive agents delivery.

Dextrin-based hydrogels are obtained from simpler, more expeditious and more economic chemical processes, when compared with other existing formulations, and do not require any toxic initiator or catalyst to trigger the crosslinking reaction. Dextrin by itself guarantees superior properties to these hydrogels, such as the capacity to be efficiently cleared from the human body, due to its low molecular weight and biodegradability.

Dextrin Oxidation

In the context of this invention, dextrin, a naturally derived polymer, is used as raw-material to produce hydrogels. Dextrin is a glucose-containing saccharide polymer linked by $\alpha$-1,4 D-glucose units, containing few (<5%) $\alpha$-1,6 links, having the same general formula as starch, but smaller and less complex.

In the present invention, a dextrin homopolysaccharide chain is oxidized using periodic acid. The periodate ion attacks one of the hydroxyl groups of the vicinal diol in dextrin residues, between C2-C3 positions of the glucopyranoside ring (FIG. 1), breaking the C—C bond and yielding two reactive aldehyde groups.

The quantification of aldehyde groups, i.e. oxidation degree (DO), can be performed using the trinitrobenzenosulfonic acid (tBC). Carbazates are well known to react with aldehydes to form stable carbazones in a similar manner to hydrazone formation, making it possible to determine the aldehyde content of dextrin by $^1$H NMR spectroscopy analysis.

The degree of oxidation of oDex can be easily controlled by the relative quantity of sodium periodate used, enabling free aldehyde reactive groups to create covalent linkages with reticulating molecules (e.g. ADH), as well as with cellular adhesion binding peptides (e.g GRGDY) or even with specific drugs for controlled delivery systems.

Gelification—oDex/ADH Hydrogel

The average polymerization degree of dextrin which is ca. 10-12. Each molecule must participate in two distinct bonds with different molecules to be efficiently reticulated. The formation of more than two bonds does not necessarily imply an enhancement on hydrogels mechanical properties (see Example 2). The excessive modification of the original polymeric chain, making available a greater number of reactive oxidized groups can be detrimental to the molecular organization of the new polymeric structure, by means of steric rearrangement hindrance. In the present invention oxidized dextrin possesses a DO between 10-50%, preferably between 25-35%, meaning an average two to three oxidized glucose residues per dextrin molecule. DOs above 50% yield very viscous solutions that react promptly with ADH, impairing good homogenization, and resulting in mat and brittle hydrogels.

Figure 3:
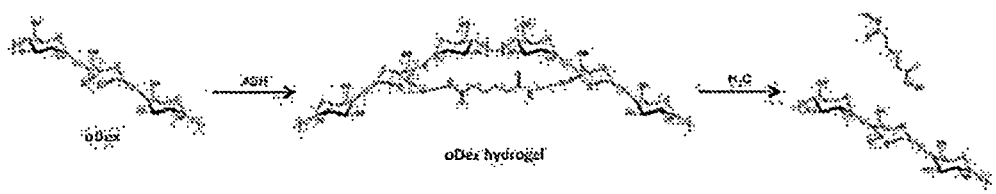
FIG. 3—Polymerization reaction of oDex with ADH and degradation products by hyrolysis.

The hydrazide groups in ADH react with the aldehyde groups in oDex and form a network of hydrolysable hydrazone bonds (FIG. 3). Once these covalent bonds are cleaved, dextrin can easily diffuse across human tissues and be eliminated via renal clearance, owing to the low molecular weight, fairly below the renal threshold (~40,000 Da). Thus, besides the naturally occurring glycosidic bonds in dextrin, the hydrazone bonds provide an additional level of control over the mechanical properties of these hydrogels. The percentage of adipic acid dihydrazide to produce the hydrogels provided by this invention situates between 3-40%, preferably between 3-10% (in molar ratio of adipic acid to oxidized dextrin residues). Example 2 shows the study of the influence of adipic acid concentration on oDex hydrogels mechanical properties. Increasing concentrations of reticulating agent result in faster crosslinking reactions and consequently impaired diffusivity of the crosslinker across the polymeric mesh. Hence, an excessive amount of ADH will not yield an homogeneous polymeric matrix with good mechanical properties. On the other hand, immoderate amounts of this homobifuntional molecule in a non-polymerized state may reveal cytotoxic. ADH concentration should thus be minimized, and optimized according to the polymer concentration and its DO.

In this invention the concentration of oxidized dextrin for the preparation of oDex hydrogels situates between 5-40% (w/v), preferably between 25-30% (w/v). Above these concentrations the solubilization of dextrin is impracticable, and below them the crosslinking times are too high (i.e., over 24 h).

It is well known that the reactivity of hydrazide groups with aldehydes is optimal at lower pH values. Under acidic conditions, aldehydes are protonated and more susceptible to nucleophilic attack by the hydrazide groups. At neutral to basic conditions, however, slower kinetics are in effect and a longer time interval is required for the completion of the reaction, yielding a lower degree of functional crosslinking. Nevertheless, dextrin-based hydrogels provided herein may be prepared at physiological pH, without compromising its mechanical properties and gelifying in 1-30 min. This suitable period of time allows for the unhurried handling and injection of the hydrogel, and its proper adjustment to the defect intended to be regenerated or site for the controlled drug release. These hydrogels do not need any special solvent—all of its components are water soluble at room temperature.

oDex/ADH Hydrogels Degradation Profiles oDex hydrogels undergo hydrolysis and crosslinked junctions are degraded along with time. The increased swelling over time is a consequence of the hydrolysis of the crosslinks (hydrazone bonds) in the hydrogel network. When the crosslinks in the hydrogel are hydrolyzed the network swells and imbibes more water, leading to further hydrolysis. Once the links are broken, dihydrazides and oxidized dextrin may diffuse across the tissues and be eliminated by the body, thanks to their low molecular weights, whereby dextrin hydrogels biodegradation profiles are especially interesting for biomedical applications, where a gradual bioabsorption of the implanted biomaterial is required, especially in cases of tissue regeneration. Example 3 presents the degradation profile studies performed on oDex/ADH hydrogels provided by this invention.

Biocompatibility

The biocompatibility of hydrogels constitutes a matter of paramount importance on the perspective of its pharmaceutical or biomedical application. A material is considered biocompatible when it verifies a complex and vast set of conditions (ISO 10993, 1992), including the absence of cytotoxicity and non-stimulation of an exacerbated inflammatory response. Generally, hydrogels present good biocompatibility. The determination of the materials cytotoxic potential may be qualitative and/or quantitative (ISO 10993-5, 1992). Qualitative evaluation is based on microscopic observation of cells, aiming to conclude about general morphology, vacuolization, cellular adhesion and membrane lysis. Quantitative evaluation in turn is based on death indexes, growth, inhibition and cellular proliferation, or colony formation. Example 4 provides the in vitro biocompatibility studies of oDex hydrogels, being applied both the evaluation methods mentioned above. Dextrin-based hydrogels provided by the present invention are non-toxic. Cells adhere and proliferate along its interface, allowing the perspectivation of a good tissue-hydrogel interaction in vivo.

Hidrogel DexOx/ADH—Bioactive Molecules and Cells

The mechanical properties of hydrogels (compression module) as well as its interaction with cells and tissues, in vivo, may be favored by the inclusion of proteins (0-20% of the hydrogels composition, dry weight) and polysaccharides (0-20% of the hydrogels composition, dry weight) on the initial formulation. The higher density obtained, associated to crosslinking effects, is likely to improve the stability in the presence of mechanical stress. Proteins such as collagen, fibronectin, casein, among others, may alter the hydrogels density, establishing bonds with oxidized groups non-reticulated through amine groups. On the other hand, proteins (e.g., collagen and fibronectin) possess peptidic sequences (e.g., RGD), promoting a more efficient cellular adhesion, which may be necessary to enhance the viability and proliferation of cells incorporated on the hydrogel, to foment tissue regeneration mechanisms, for instance, through growth factors delivery. The use of polysaccharides such as chitosan or hyaluronic acid, among others, allow the variation of the hydrogels surface charge, making it positive or negative, respectively. Additionally, the selection of the molecular weight of the polysaccharides used (degradable for the mentioned cases) enables the modulation of the hydrogels mechanical properties and degradation profiles.

Hidrogel DexOx/ADH—Nanogel

The incorporation of nanogels, made of modified dextrin, mannan, chitosan or hyaluronic acid, but not only, obtained by self-assembling through the grafted hydrophobic moieties, allow the incorporation in the hydrogel of a nanodispersed hydrophobic phase, build up of hydrophobic cores allowing the dissolution of poorly water soluble pharmaceuticals. The incorporation of the nanogel in the hydrogel is carried out by mixing the nanogel with the oxidized dextrin, previous to the addition of ADH (see Example 5). The nanogel may be previously loaded with pharmaceuticals (e.g. statines, anti-inflammatory drugs or, virtually, any hydrophobic molecule). The use of the nanogel allows in a facile way the incorporation of molecules which, being poorly water soluble, hardly would be incorporated in the hydrated environment of a hydrogel. On the other hand, the nanophase of the hydrophobic cores perform as a controlled release system. The release is controlled, in this system, not only by the mass transfer by diffusion and gel degradation rate. The use of nanogels with different dimensions (10-10000 nm, according to the polysaccharide used), allows an additional control over the release of the pharmaceuticals.

Nanogel particles can act as a drug reservoir from which release can be triggered by a stimulus (to which they are sensitive), or simply released in a diffusion-controlled manner. Simultaneous diffusion of molecules of different nature can be obtained from the same platform, by adding two (or more) different populations of nanogels loaded with different drugs in the same hydrogel matrix, where the release rate of each solute is controlled via the interaction between the hydrogel and the nanogels. The major advantage relies on the improvement of the kinetic release profile of the drug, as the hydrogel phase provides an additional diffusion barrier moderating or eliminating the initial burst release typical observed in hydrogel or nanogel drug delivery systems.

EXAMPLES

Hereinafter, the present invention is described in more detail and specifically with reference to the Examples, which however are not intended to limit the present invention.

Example 1

Hydrogel oDex/ADH

Dextrin Oxidation. Aqueous solutions of dextrin (2% w/v) were oxidized with a 2 mL sodium m-periodate solution (Panreac), whose concentration varied according to the desired theoretical degree of oxidation (DOt). The flasks were wrapped in aluminum foil and the reaction was stirred for 20 h at room temperature, after which an equimolar amount of diethylene glycol was added dropwise to reduce any unreacted periodate. The resulting solution was dialyzed for 3 days against water, using a dialysis membrane with a MWCO 1000 Da, and then lyophilized for 10 days (FIG. 1).

Determination of Aldehyde Groups by $^1$H NMR Analysis. The degree of oxidation (DO) of oDex is defined as the number of oxidized residues per 100 glucose residues, quantified using the tert-butylcarbazate (tBC). oDex was dissolved in phosphate buffer pH 6.0, 0.1M (1 mL, 1% w/v), subsequently a 5-fold excess of tBC was dissolved in the same buffer (1 mL) and added separately. The mixture was allowed to react for 24 h at room temperature. Excess low-molecular weigh tBC was then removed using a PD-10 desalting column system and the filtrate was lyophilized for 48 h. Afterwards the resulting product was dissolved in deuterated water (D2O) (7.5 mg/ml) and analyzed by $^1$H NMR. The 1H NMR spectrum was used to determine DO calculated as a peak area ration in the NMR spectra according to equation 1.

$$DO(\%) = (X/Y) \times 100 \qquad \text{(Eq. 1)}$$

Where, X is the average integral at δ 7.3 ppm corresponding to the protons connected to the carbons which were modified with tBC and Y is the average integral of the anomeric protons at δ 4.8 ppm and δ 5.4 ppm Preparation of oDex-ADH Hydrogels. oDex was dissolved in phosphate buffer pH 6.0, 0.1M (30% w/v) at room temperature and an adipic acid dihydrazide (ADH) solution (prepared separately) was added at different concentrations (5%, 15% and 30% in molar base, taking into account the number of glucose residues in the original dextrin). The crosslinking reaction was allowed to proceed during 2 h. The material was considered gelified when it stopped slipping along an 90° inclined surface.

Figure 2:
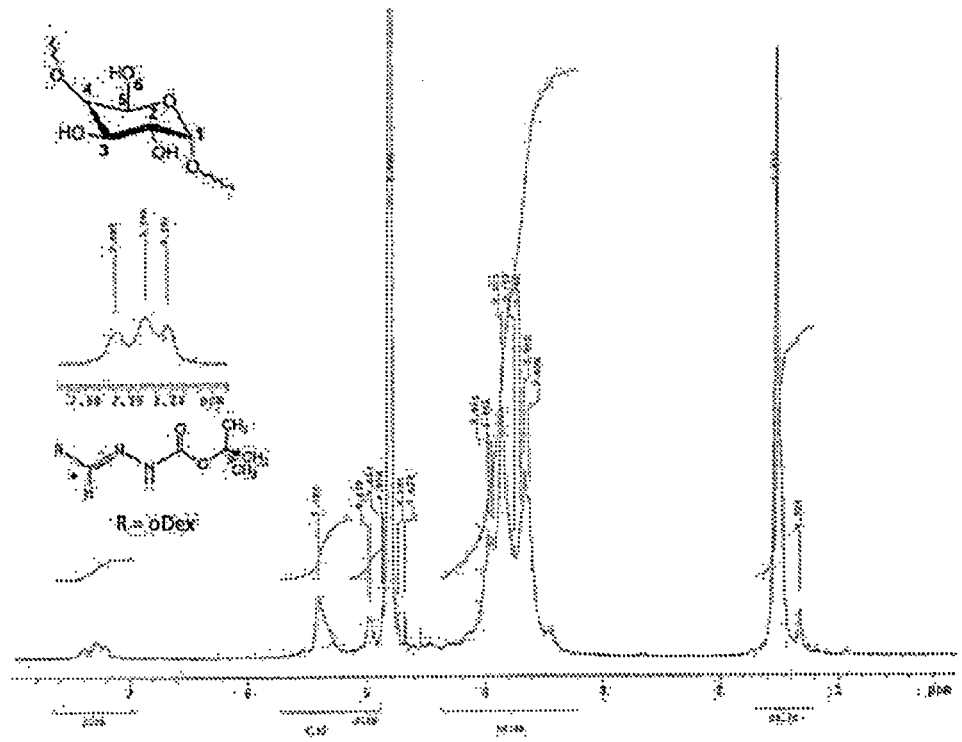
FIG. 2—Oxidized dextrin (DO 25%) $^1$H NMR spectrum.

FIG. 2 depicts a typical $^1$H NMR spectra obtained for 25% oxidized dextrin (oDex 25%). The peaks between δ 4.0 and δ 3.4 ppm are assigned to protons at positions 2, 3, 4, 5 and 6, while the peak at δ 5.4 ppm is attributed to the anomeric proton from the glucose unit. The spectrum also shows a small peak at δ 5.3 ppm corresponding to the anomeric proton in dextrin with α-1,6 linkages. The three peaks between δ 7.4 and δ 7.2 ppm are assigned to the proton attached to the carbon that was modified with tBC, and the singlet at δ 1.5 ppm assigned to tBC.

To evaluate the gelification profile of oDex hydrogels, the solubility of oDex was accessed. Several oDex polymer solutions with different concentrations were prepared in phosphate buffer pH 6.0. It was noticed that above 30% (w/v) solutions were extremely viscous and practically impossible to homogenize. So, this concentration was considered as the threshold of oDex solubility in phosphate buffer pH 6.0, and was further on applied in the synthesis of all oDex hydrogels. Next, oDex was crosslinked with various concentrations of adipic dihydrazide (FIG. 3). Twelve hydrogel samples were initially produced with DOs varying from 25% to 50% and ADH concentrations between 5% and 30% (in molar ratio, taking into account the number of glucose residues in the original dextrin).

Figure 4:
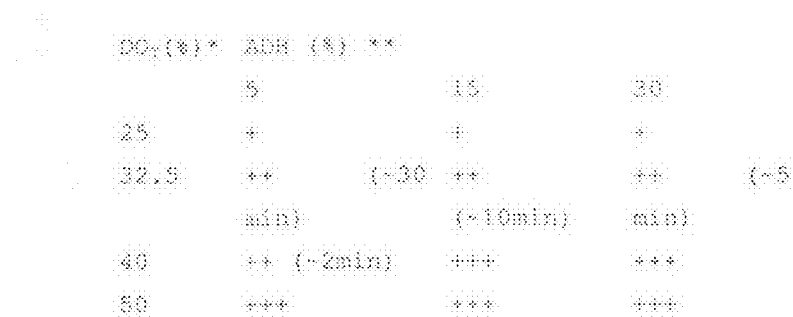
FIG. 4—Variation of crosslinking times with the degree of oxidation and adipic acid dihydrazide concentration. (+) over 1 h gelation (++) gelation in less than 30 min (+++) gelation in less than 1 min. The material was considered gelified when it stopped slipping along an 90° inclined surface. * Calculated as the molar ration of sodium periodate per initial glucose unit in dextrin. ** Calculated in molar base, taking into account the number of glucose residues in the original dextrin.

FIG. 4 shows the approximate gelation periods obtained. As expected the crosslinking times decrease with increasing DOs, as well as with increasing amounts of reticulating agent. It was found that DOs above 40% yield very viscous solutions that react promptly with ADH, impairing good homogenization, and resulting in mat and brittle hydrogels. Through control of DO and ADH concentrations, a good control over the gelification time is thus possible, making this hydrogel suitable as an injectable system.

Example 2

Mechanical Properties

The mechanical properties of crosslinked dextrin hydrogels were assessed using a Mechanical Tester—Shimadzu-AG-IS 1 kN Testing Instrument. Each hydrogel disc (superficial area=133 mm$^2$) was placed between two parallel metallic circumferential plates, so that the compressive force would be uniform along the sample, and compressed at room temperature with a constant deformation rate of 0.5 mm min$^{-1}$. The compressive modulus of hydrogels is directly proportional to the intermolecular crosslink density. Hence, the influence of the ADH concentration, DO and also the type of solvent used on the extent of intermolecular crosslinking was evaluated by quantifying the compressive modulus of oDex hydrogels.

Figure 5:
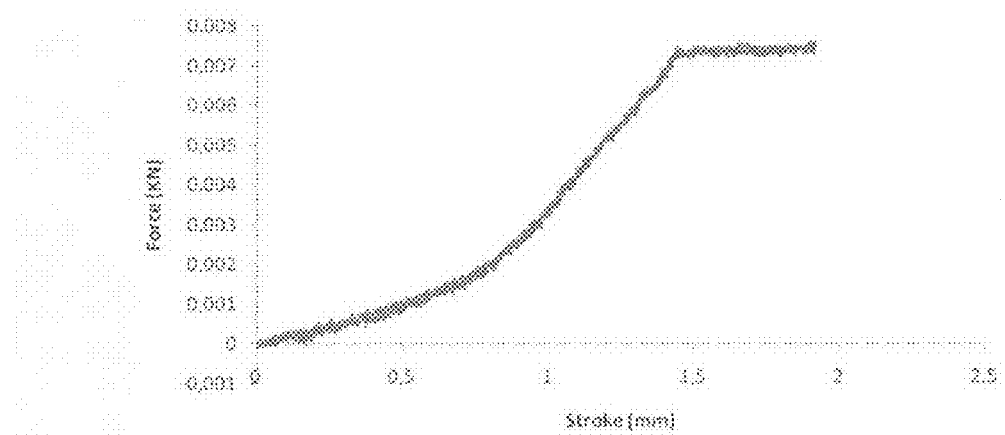
FIG. 5—Compression curve showing typical behavior for a oDex DO 35% with 4% ADH hydrogel.

FIG. 5 presents a typical compression curve obtained for oDex hydrogels, from which the compressive modulus was determined, using equation 2:

$$\text{Compressive modulus(KPa)} = (\text{Stress max/Superficial area}) \times 10^{-3} \quad (Eq. 2)$$

Figure 6:
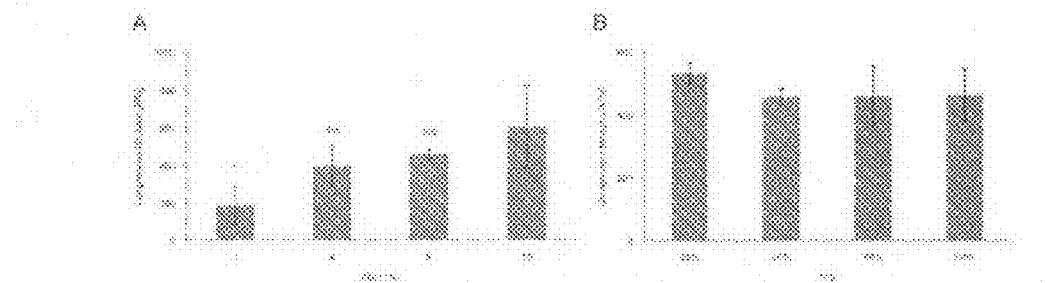
FIG. 6—Compressive modulus of (A) crosslinked oDex hydrogels as a function of the ADH concentration (in molar ratio, taking into account the number of glucose residues in the original dextrin, oDex DO 35% (30% w/v) in 0.1 M phosphate buffer, pH 6.0), and (B) crosslinked oDex hydrogels as a function of the degree of oxidation of dextrin (oDex DO 35% and 5% ADH in 0.1 M phosphate buffer, pH 6.0). Results presented as average±SD, n=3. ns: non-significant, p>0.05; ** p<0.01, compared to the highest concentration of ADH used.
Figure 7:
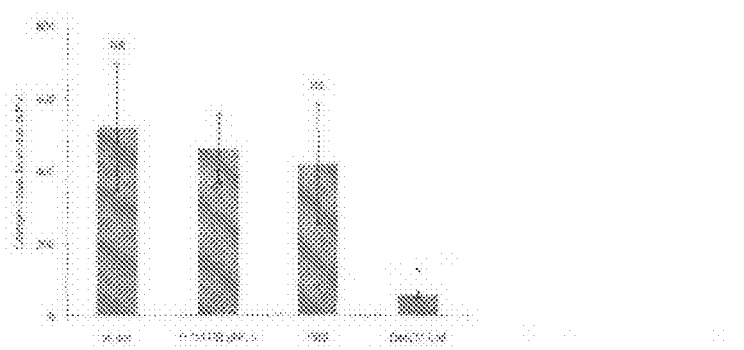
FIG. 7—Compressive modulus of crosslinked oDex hydrogels as a function of the solvent in which they are prepared. All hydrogels were prepared with oDex (30% w/v) and 5% ADH. Results presented as average±SD, n=3. ns: non-significant, p>0.05; * p<0.05, compared to the solvent in which hydrogels are normally synthesized (0.1M phosphate buffer, pH 6.0).

For each condition, samples in triplicate were analyzed; the values given in FIGS. 6 and 7 represent the mean and the standard deviation.

The increasing concentration of ADH resulted in an increase in the compressive modulus of crosslinked oDex hydrogels (FIG. 6A), suggesting the establishment of an increasing number of intermolecular bonds as more hydrazide groups become available to react. The same tendency was reported by Maia et al. (2005) with dextran hydrogels and by Bouhadir et al. (1999) with poly(aldehyde guluronate) hydrogels, the former revealing inferior compressive strength even with higher concentrations of reticulating agent. In fact, the maximum compressive modulus obtained with guluronate hydrogels was 560 KPa, with 150 mM ADH, while with ca. 130 mM (equivalent to 10% in molar ratio) a compressive modulus of 600 KPa for oDex 35% hydrogels was registered. Thus, dextrin hydrogels appear to have better mechanical properties.

The influence of the degree of oxidation on the intermolecular crosslinks was evaluated, and no direct proportionality relationship between the compressive modulus and the DO was identified. oDex DO 25% hydrogels revealed the maximum compressive force (c.a. 533 KPa), although there was no significant difference (p>0.05) relatively to higher DO oDex hydrogels (FIG. 6B).

Injectable hydrogels should be able to prosecute its polymerization process in situ, meaning the interstitial fluids and/or blood should not interfere with it, for instance by influence of the media pH. Also, the intrinsic conditions necessary for the hydrogel's formation must not be harmful to the surrounding tissues. Hence, the pH influence on the density of intermolecular bonds was evaluated by measuring the compressive modulus of various oDex hydrogels prepared in four different solvents: dd water (c.a pH 5.77), 0.1M phosphate buffer (pH 6.0), PBS (pH 7.4) and cDMEM (c.a pH 7.5), respectively. Results are shown in FIG. 7. In fact, it is well known that the reactivity of hydrazide groups with aldehydes is optimal at lower pH values. Under acidic conditions, aldehydes are protonated and more susceptible to nucleophilic attack by the hydrazide groups. At neutral to basic conditions, however, slower kinetics are in effect and a longer time interval is required for the completion of the reaction, yielding a lower degree of functional crosslinking. A possible explanation for the low compressive modulus values (58 KPa) of hydrogels prepared in cDMEM, could be assigned to the presence of aminoacids in solution, which might be interacting with aldehyde groups in oDex, following hydrolysis of hidrazone bonds.

Example 3

Biocompatibility

The cell cytotoxicity was evaluated for un-crosslinked macromonomer solutions, crosslinked hydrogels and hydrogel degradation extracts using Live and Dead® and MTT assays, as described below.

Mouse Embryo Fibroblasts 3T3 Culture. Mouse embryo fibroblasts 3T3 (ATCC CCL-164) were grown in Dulbecco's modified Eagle's media (Sigma) supplemented with 10% newborn calf serum (Invitrogen, UK) and 1 µg/ml penicillin/streptavidin (DMEM complete medium) at 37° C. in a 95% humidified air containing 5% CO2. At 80% confluency, 3T3 fibroblasts were harvested with 0.05% (w/v) trypsin-EDTA and subcultivated in the same medium.

Live and Dead Assay. The LIVE/DEAD® Viability/Cytotoxicity Kit for mammalian cells (Invitrogen, UK) was used to determine cell viability. This kit provides two-colour fluorescence cell viability assay, based on the simultaneous determination of live and dead cells with two probes that measure intracellular esterase activity and plasma membrane integrity.

Mousse embryo fibroblasts 3T3 were seeded ($5 \times 10^4$ cells/well) in a 6 well polystyrene plate (Orange Scientific) and incubated at 37° C., 5% $CO_2$ for 24 hours. Then, the culture medium was removed and hydrogel discs (Ø4 mm, 2 mm thickness) were placed on the wells, in direct contact with cells. At regular time intervals, 200 µL of a solution of 2 µM calcein AM and 4 µM ethidium homodimer-1, in sterile PBS, were added to the wells, incubated for 30 to 45 minutes at 37° C., 5% CO2 (as indicated by the manufacturer) and visualized in a fluorescence microscope. Latex discs and agar gel (U.S. Pharmacopeia) were used as positive and negative controls, respectively.

MTT. The viability of the 3T3 fibroblast cells was determined using 3-[4,5-dimethylthiazol-2-yl]-2,5-diphenyl tetrazolium bromide (MTT) assay (Sigma-Aldrich, USA). The MTT assay accurately measure the activity of living cells via mitochondrial dehydrogenase activity. Mitochondrial dehydrogenases of viable cells cleave the tetrazolium ring, yielding purple MTT formazon crystals that can be dissolved in DMSO, resulting in a purple solution that is spectrophotometrically measured. The increase in cell number results in an increase in absorbance.

The fibroblasts adhesion to oDex hydrogels was also evaluated, by MTT assay. For this assay, oDEx hydrogels were formed at the bottom of the wells of a 96 well polystyrene culture plate. After 2 h of polymerization, the oDex hydrogels were washed with PBS and three times with cDMEM. Then, 3T3 fibroblasts cells were added ($3 \times 10^3$ cells/well) to each well. The culture medium was refreshed every 2 days. For the control assays, cells were grown directly in the bottom of the wells. After 48 h, hydrogels were carefully washed three times with PBS, to remove floating cells, and the cell layer was detached before conducting the MTT assay.

The biocompatibility of the hydrogels degradation extracts was also evaluated. In a few words, 3T3 fibroblasts cells were seeded ($5×10^2$ cells/well) in a 96 well polystyrene plate and exposed to hydrogel degradation extracts (200 μL; 1:1, 1:2 and 1:4 dilutions) obtained separately from three oDex hydrogels (DO 40%). After 48 h of incubation at 37° C., the cytotoxicity of the extracts was evaluated using the MTT assay.

Furthermore, oxidized dextrin and ADH alone were also tested for their cytotoxic potential. Briefly, 3T3 cells ($5×10^2$ cells/well) seeded in a 96 well polystyrene plate were exposed to increasing concentrations of these components for 48 h at 37° C., after which the cytotoxicity was evaluated using the MTT assay. Oxidized dextrin was firstly sterilized by ethylene oxide (ETO) sterilization process. All biocompatibility measurements were made in triplicate or more and the results given are the mean.

Figure 8:
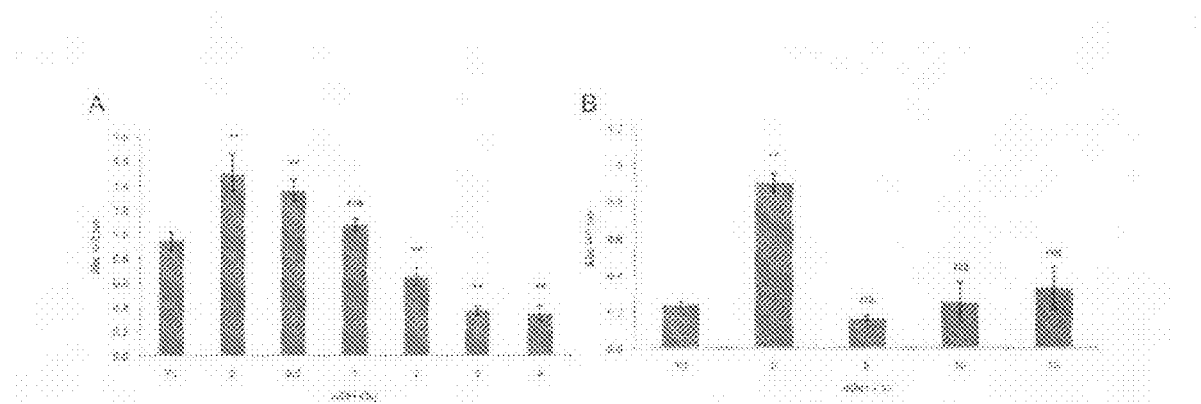
FIG. 8—MTT absorbance values obtained after 48 h incubation of 3T3 cells in direct contact with (A) different concentrations of reticulating agent (ADH) alone, and (B) different concentrations of oxidized dextrin alone. Results presented as average±SD, n=3. ** p<0.01, compared to the T0 control (24 h after cell seeding).

FIGS. 8A and 8B depict the MTT absorbance values obtained after 48 hours incubation with different concentrations of ADH and oDex, respectively. After 48 hours incubation, higher concentrations of ADH (2-4% w/v) induce cell death. However, when the amount of ADH used to form the oDex hydrogels (5% molar base corresponding to 1% w/v) is incubated with 3T3 fibroblasts no significant difference is noted in MTT absorbance values. Additionally, oDex does not induce cell death, although proliferation is not observed in the presence of the material. Altogether, the results points to a high level of compatibility of the amount of ADH and oDex used for the oDex hydrogel production.

Figure 9:
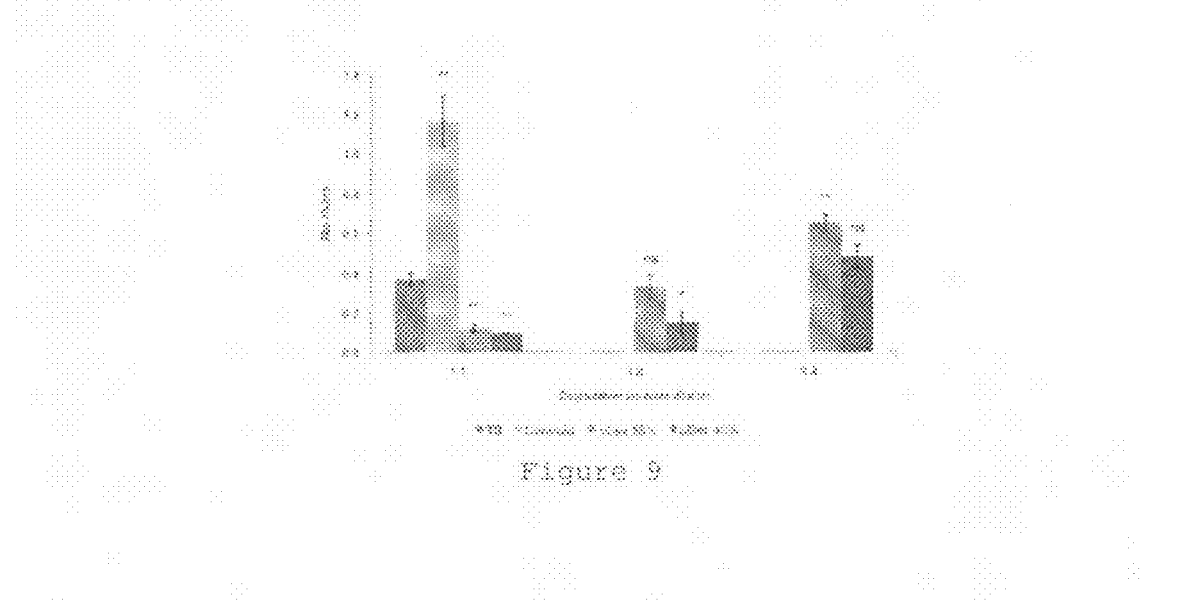
FIG. 9—MTT absorbance values obtained after 48 h incubation of 3T3 cells with degradation products (1:1, 1:2 and 1:4 dilutions) of oDex (DO 35% and 40%) hydrogels. Results presented as average±SD, n=3. Ns: non-significant, p>0.05; *p<0.05; ** p<0.01, compared to the T0 control.

The products of the hydrogels degradation can be potentially cytotoxic; in order to evaluate its toxicity, the extracts obtained during degradation oDex hydrogel were incubated with mouse embryo fibroblasts 3T3 cells and MTT assay was used to measure 3T3 fibroblasts cellular viability. The results are shown in FIG. 9.

Figure 10:
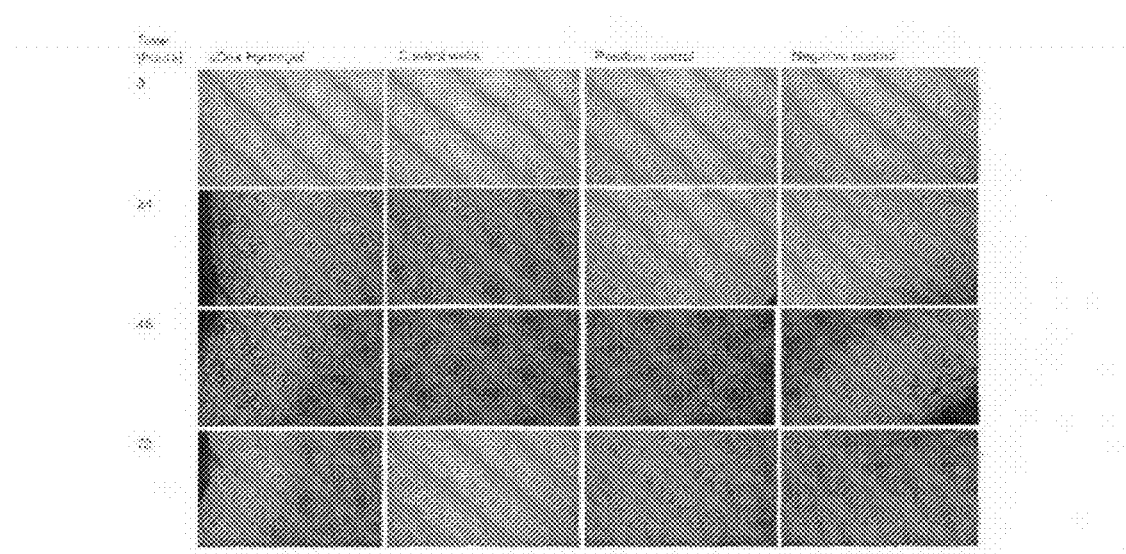
FIG. 10—Morphologic evaluation of 3T3 cells in direct contact with dextrin hydrogels (DO 35%), TCPS cell culture plates (control), agarose gel (negative control) and latex rubber (positive control). 10× magnification. Dark shadows on the left side show part of hydrogel or latex disc.

Cellular death is observed when the oDex degradation products are in direct contact with cells, although this effect attenuates as the degradation products are diluted. In the wells where the degradation products are used (dilution 1:1), sedimentation of these degradation products was observed. This fact suggests that cellular death could be caused by the mechanical pressure or by the diminished oxygenation and nutrient diffusion caused by the products sedimentation. To evaluate oDex cytotoxicity, the Live and Dead® assay was also performed. oDex (DO 35%) hydrogels were placed in direct contact with cells and latex discs and agar gels were used as positive and negative controls, respectively. As expected, latex discs revealed high toxicity, for cells are majorly red (dead cells). On the contrary, with agar discs and oDex hydrogels the majority of cells are alive (green cells). As FIG. 10 illustrates, oDex hydrogels does not inhibit cell proliferation. Although the number of cells is inferior comparing to control wells, cells are adherent and retain the typical fibroblast morphology.

Figure 11:
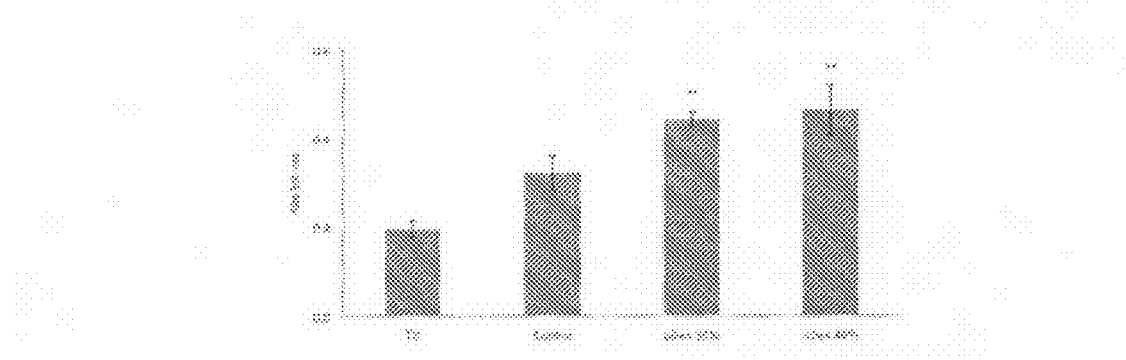
FIG. 11—MTT absorbance values obtained after 48 h incubation of 3T3 cells on oDex (DO 35% and 40%) hydrogels. Results presented as average±SD, n=3. ** p<0.01, compared to the T0 control.

To evaluate the effects of the oDex hydrogels on the adhesion of mouse embryo fibroblasts 3T3, oDex (DO 35% and 40%) hydrogels were formed on the bottom of polystyrene wells and then cells were seeded. Polystyrene wells were used as control. The cellular adhesion was evaluated with MTT ((3-(4,5-Dimethylthiazol-2-yl)-2,5-diphenyltetrazolium bromide) test. As seen in FIG. 11, after 48 hours incubation the number of adhered cells is significantly higher in both oDex hydrogels comparing to the control (polystyrene wells). This is a somewhat unexpected and rather interesting result, since in other dextrin hydrogels developed in our lab, an improved proliferation as compared to polystyrene was not observed.

Example 4 oDex/ADH Hydrogel—Dextrin Nanogel

Dextrin nanogel was prepared: the self-assembled hydrogel nanoparticles were obtained by dissolving the lyophilized dextrin with grafted acrylate groups (VA), substituted with hydrophobic 1-hexadecanethiol ($C_{16}$) (dextrin-VMA-$SC_{16}$) in PBS. The dissolution was accomplished after approximately 16 hours at room temperature, with stirring. The nanogel formation was confirmed by dynamic light scattering. oDex, DO 35%, (30% w/v) was dissolved in PBS (oDex) or in a suspension of nanogel (oDex-nanogel) for approximately 16 hours at room temperature. Then, the oDex suspensions were mixed with 5% (in molar base taking into account the number of glucose residues in the original dextrin) adipic acid dihydrazide with the pipette tip. The crosslinking was allowed to proceed at room temperature for about 2 hours.

Example 5 oDex/ADH Hydrogel Degradation Profile and Dextrin Nanogel/FITC Release

After being prepared and weighted ($W_i$), the hydrogels were immersed in PBS or DMEM, and incubated at 37° C. At regular intervals, they were removed from the solutions, blotted with filter paper, weighed ($W_t$) and returned to the same container. The buffer solution was replaced at each measurement and the old stored for further analysis. The percentage of mass loss was determined using the equation (equation 3):

$$\text{Mass loss}(\%) = 100 - [(W_t/W_i) \times 100] \quad \text{(Eq. 3)}$$

Preparation of FITC Labeled Dextrin Nanogel. FITC is a fluorescent probe commonly used in biological studies, owing to its biocompatibility. To obtain nanogels labeled with FITC, a nanogel (prepared as described below in Example 6 and in Gonçalves et al., 2007) solution was formed by dissolving 10 mg of dextrin-VMA-SC16 in 1.3 ml 0.1M sodium phosphate buffer pH 7 and stirred for 30 min. Simultaneously, a fluorescein solution was prepared by dissolving 5 mg of SAMSA [(5-(2-(and-3)-S-(acetylmercapto)succinoyl)amino)Invitrogen]flourescein in 0.5 ml of 0.1 M NaOH and stirred for 15 min. Then, 7 μl of 6M HCl and 0.1 ml of 0.5M NaPO4 buffer pH 7 were added and stirred for 10 min. Finally, the nanogel solution and the fluorescein solution were mixed and stirred for 30 min. Unbound FITC was separated using a Sephadex G25 PD10 column (Amersham Biosciences) equilibrated with PBS, and the labelled nanogel (nanogel/FITC) was eluted with PBS.

Evaluation of the Dextrin Nanogel/FITC Release. The oDex-nanogel/FITC hydrogel was obtained as described previously (preparation of oDex-nanogel hydrogel). The nanogel/FITC release from the oDex-nanogel hydrogels was evaluated by fluorimetry. The fluorescence intensity of the PBS removed from the hydrogels, at regular intervals, was measured using a spectrofluorimeter (Fluorolog Horiba Jobin Yvon). Fluorescence spectra were collected using an excitation wavelength of 460 nm and recording emission between 470 and 600 nm at 1 nm intervals. The slit width was set at 6.0 nm for the excitation and emission. The fluorescence intensity was measured at the maximum of the peak obtained (520 nm). The percentage of nanogel/FITC released from the oDex-nanogel hydrogel was obtained by equation 4:

Nanogel/FITC release(%)=[nanogel/FITC]$_{det}$/[nanogel/FITC]$_{tot}$×100     (Eq. 4)

where, [nanogel/FITC]$_{det}$ is the fluorescence intensity detected in the PBS collected at determined time and [nanogel/FITC]$_{tot}$ is the fluorescence intensity of the total nanogel/FITC incorporated in the oDex hydrogel.

Depending on the chemical structure of the polymer backbone, hydrogel degradation can occur by either surface or bulk erosion. Surface erosion takes place when the rate of erosion exceeds the rate of water permeation into the bulk of the polymer. Bulk erosion occurs when water molecules permeate into the bulk of the matrix at a faster rate than erosion, thus exhibiting a complex degradation/erosion kinetics. In oDex hydrogels, degradation mainly occurs by bulk erosion and it is characterized by non-linear degradation profile accompanied by an increasing pore size, as seen in FIGS. 13A and 13B. The variation in pore size during the degradation of the hydrogel network is important since it affects the swelling of the hydrogel, the diffusion of molecules, and the delivery of cells when the hydrogels are used for cell encapsulation.

Figure 13:
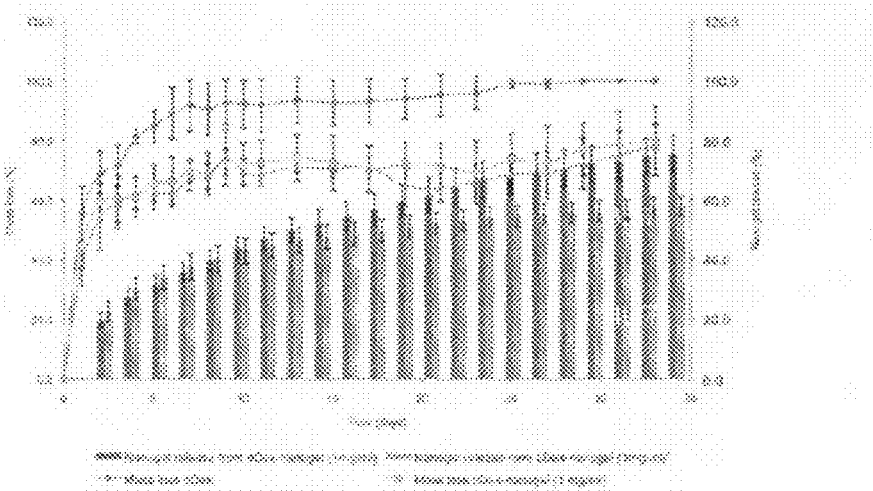
FIG. 13—Mass loss and nanogel cumulative release profiles of oDex, oDex-nanogel (1 mg/ml) and oDex-nanogel (3 mg/ml). Shown are mean±SD, n=6.

This Example also shows the studies on the release profile of dextrin nanogels imbebed in oDex/ADH hydrogels (FIG. 13). Dextrin nanogels are produced according to Example 6, and have a similar degradation profile to oDex/ADH hydrogels.

Figure 12:
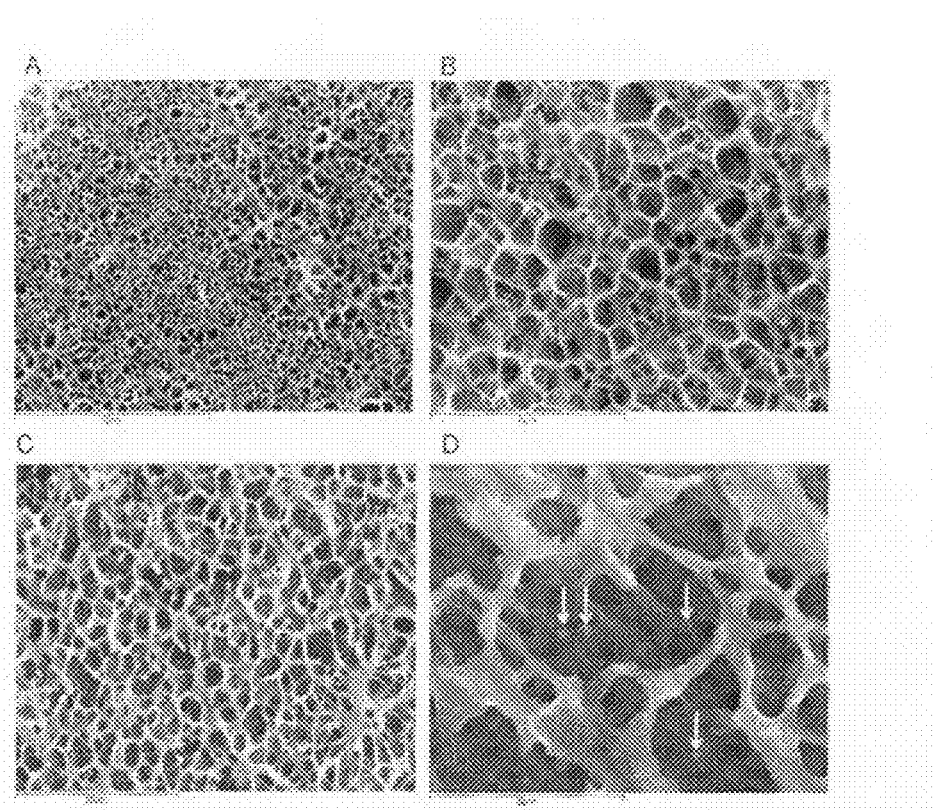
FIG. 12—Cryo-SEM images from cross-section of oDex hydrogel (A) before and (B) after immersion on PBS buffer for 24 hours and (C, D) oDex-nanogel hydrogel. Arrows show the dextrin nanogels (oDex DO 35%).

The morphology of the oDex hydrogels (examined by Cryo-SEM—FIG. 12) exhibit a continuous porous structure, with a diameter of about 1 μm. With a larger amplification, the nanogel particles present in oDex-nanogel hydrogel can be observed. No obvious morphologic differences are noticeable comparing the oDex and oDex-nanogel hydrogel formulations. All hydrogels have random morphology and similar porous structure and the incorporated nanogels did not have significant influence in the morphology of the oDex hydrogel network.

In spite of their many favorable properties, hydrogels also have some limitations. The low tensile strength limits their use in load-bearing applications and, as a consequence, the premature dissolution or flow away of the hydrogel from the targeted local site can occur. Concerning drug delivery, the most important drawback of hydrogels relates to the quantity and homogeneity of drug loading, which may be limited, especially in the case of hydrophobic drugs; on the other hand, the high water content and large pores frequently result in relatively rapid drug release. In order to surmount these limitations, the dextrin nanogel also provided by this invention can be used to produce a new bidimensional hydrogel. Since this nanogel is obtained by self-assembling of amphiphilic molecules, and have been shown to incorporate and stabilize both proteins and small hydrophobic pharmaceuticals, the presence of the nanophase may be useful for the development of the material as a controlled drug release system.

According to mass loss studies performed, the degradation speed of oDex hydrogel is different from the one found in oDex-nanogel hydrogels. In approximately 25 days, the oDex hydrogel network is completely solubilized, on the other hand at this time only about 70% mass loss was observed in oDex-nanogel hydrogels. However, only a slight difference in mass loss is observed comparing the two formulations with different amounts of nanogel. The slower degradation rate observed in the presence of the nanogel may be assigned to a further reticulation of the hydrogel network.

Simultaneously, the nanogel (previously labeled with FITC) release from the oDex-nanogel hydrogels was evaluated by fluorimetry. The nanogel was gradually released over time, paralleling the hydrogel degradation. The composite oDex-nanogel hydrogel could be useful to overcome the initial burst release phenomenon often observed in nanogel drug delivery systems as it allows for the nanogel slow and controlled release.

References

Patents

Colin Brown, US2010/0240607A1, Dextrin-containing composition for preventing surgical adhesions Isabella Orienti and Elena Paolini, WO2009/016663A1, Amphiphilic dextrin conjugates and their use in pharmaceutical formulations as complexing agents for hydrophobic drugs to improve the aqueous solubility and consequently the therapeutic efficacy of the complexed drugs Kamal Bouhadir, Genevieve Kruger and David Mooney, US2007/07186413, Hydrogels and water soluble polymeric carriers for drug delivery Karen Burg, US2006/6,991,652 B2, Tissue engineering composite Kazunari Akiyoshi, Matsuda Osamu, Kishida Tusanao, Shimizu Takeshi, JP2009/149526A2: Sustained release preparation for subcutaneous or intramuscular injection, containing cytokine-nanogel composite Kazunari Akiyoshi, Morimoto Nobuyuki, Iwasaki Yasuhiko, JP2005/298644A2, Preparation of hybrid gel for conveyance of bioactive substance, involves copolymerizing functional monomer with compound obtained by introducing polymerizable group to water-soluble polysaccharide Peter Unger and Ronald Rohrbach, US1996/5541234, Process for making low density hydrogel material having high surface areas.

Ronald Hill, Richard Klann, Francis Lamberti, WO2005/042048A2, Methods and compositions for regenerating connective tissue Other References Hreczuk-hirst D, Chicco D, German L, Duncan R. Dextrins as potential carriers for drug targeting: tailored rates of dextrin degradation by introduction of pendant groups. *International Journal of Pharmaceutics*. 2001; 230:57-66.

Drury J L, Mooney D J. Hydrogels for tissue engineering: scaffold design variables and applications. *Biomaterials*. 2003; 24:4337-4351.

Nogusa H, Yano T, Okuno S, Hamana H, Inoue K. Synthesis of carboxymethylpullulan peptide doxorubicin conjugates and their properties. *Chem. Pharm. Bull.* 1995; (43):1931-1936.

Nishikawa M. Pharmacokinetic evaluation of polymeric carriers. *Advanced Drug Delivery Reviews*. 1996; 21(2):135-155. Available at: http://linkinghub.elsevier.com/retrieve/pii/S0169409X96004036.

Vercauteren R, Bruneel D, Schacht E, Duncan R. Effect of the Chemical Modification of Dextran on the Degradation by Dextranase. *J. of Bioactive and Comp. Polymers.* 1990; 5:4-15.

Danauser-Reidl S, Hausmann E, Schick H, et al. Phase-I clinical and pharmacokinetic trial of dextran conjugated doxorubicin (AD-70, DOX-OXD). *Invest. New Drugs*. 1993; (11):187-195.

Treetharnmathurot B, Dieudonné L, Ferguson E L, et al. Dextrin-trypsin and ST-HPMA-trypsin conjugates: enzyme activity, autolysis and thermal stability. *International journal of pharmaceutics*. 2009; 373(1-2):68-76. Available at: http://www.ncbi.nlm.nih.gov/pubmed/19429290.

Kerr, D. J., Young, A. M., Neoptolemos, J. P., Sherman M, Van-Geene, P., Stanley, A., Ferry, D., Dobbie J W, Vincke, B., Gilbert, J., El Eini, D., Dombros, N. F-, Las G. Prolonged intraperitoneal infusion of 5-fluorouracil using a novel carrier solution. *Br. J. Cancer.* 1996; 74:2032-2035.

Davtyan T, Hakobyan I, Muradyan R, Hovhannisyan H, Gabrielyan E. Evaluation of amino acids as mediators for the antibacterial activity of iodine-lithium-α-dextrin in vitro and in vivo. *J Antimicrob Chemother.* 2007; (59):1114-1122.

Avetisyan S, Hakobyan G, Davtyan T. Modulation of endotoxin-induced respiratory splash of granulocytes and monocytes in patients with familial Mediterranean fever by iodine-lithium-α-dextrin and sodium thiosulfate. *Patol Fiziol Eksp Ter.* 2006; (1):11-13.

Asai, T., Hayashi, T., Hamajima, S., Mieki, A., Kataoka, H., Kawai T. Development of Bone Filling Material made from the Dextrin Complex American Association for Dental Research, Miami, Fla. 2009.

Carvalho J, Gonçalves C, Gil A M, Gama F M. Production and characterization of a new dextrin based hydrogel. *European Polymer Journal.* 2007; (May).

Luz, P. P., Neri, C. R., Serra O A. Dextrin-Microencapsulated Porphyrin: Luminescent Properties. *Annals of the New York Academy of Sciences.* 2008; 1130:91-96.

Davies D S. Kinetics of icodextrin. *Perit. Dial. Int.* 1994; 14:S45-S50.

Bouhadir K H, Hausman D S, Mooney D J. Synthesis of cross-linked poly(aldehyde guluronate) hydrogels. 1999; 40:3575-3584.

Jia X, Burdick J a, Kobler J, et al. Synthesis and Characterization of in Situ Cross-Linkable Hyaluronic Acid-Based Hydrogels with Potential Application for Vocal Fold Regeneration. *Macromolecules.* 2004; 37(9):3239-3248. Available at: http://pubs.acs.org/doi/abs/10.1021/ma035970w.

Goncalves, C., Martins, J. A., Gama F M. Self-assembled nanoparticles of dextrin substituted with hexadeanethiol. *Biomacromolecules.* 2007; 8(2):392-398.

Gonçalves, C., Gama F M. Characterization of the self-assembly process of hydrophobically modified dextrin. *European Polymer Journal.* 2008; 44(11):3529-3534.

Anseth K S, Bowman C N, Brannon-Peppas L. Mechanical properties of hydrogels and their experimental determination. *Biomaterials.* 1996; 17(17):1647-1657. Available at: http://linkinghub.elsevier.com/retrieve/pii/0142961296876447.

Maia J, Ferreira L, Carvalho R, Ramos M A, Gil M H. Synthesis and characterization of new injectable and degradable dextran-based hydrogels. *Polymer.* 2005; 46:9604-9614.

Massia S P, Stark J. Immobilized RGD peptides on surface-grafted dextran promote biospecific cell attachment. *Journal of biomedical materials research.* 2001; 56(3):390-9. Available at: http://www.ncbi.nlm.nih.gov/pubmed/11372057.

Ferreira L, Rafael A, Lamghari M, et al. Biocompatibility of chemoenzymatically derived dextran-acrylate hydrogels. *Journal of biomedical materials research. Part A.* 2004; 68(3):584-96. Available at: http://www.ncbi.nlm.nih.gov/pubmed/14762939.

Carvalho J, Moreira S, Maia J, Gama F M. Characterization of dextrin-based hydrogels: Rheology, biocompatibility, and degradation. *Journal of Biomedical Materials Research Part A.* 2010 April; 93(1):389-99.

Moreira, S; Costa, R; Guardão L.; Gärtner F.; Vilanova M.; Gama M. In Vivo Biocompatibility and Biodegradability of Dextrin-based Hydrogels. *Journal of Bioactive and Compatible Polymers.* 2010; 25(2):141-153.

Maia J, Ribeiro M P, Ventura C, et al. Ocular injectable formulation assessment for oxidized dextran-based hydrogels. *Acta biomaterialia.* 2009; 5(6):1948-55. Available at: http://www.ncbi.nlm.nih.gov/pubmed/19286432.

Chen Y M, Shiraishi N, Satokawa H, et al. Cultivation of endothelial cells on adhesive protein-free synthetic polymer gels. *Biomaterials.* 2005; 26(22):4588-96. Available at: http://www.ncbi.nlm.nih.gov/pubmed/15722128.

Schneider G B, English A, Abraham M, et al. The effect of hydrogel charge density on cell attachment. *Biomaterials.* 2004; 25(15):3023-8. Available at: http://www.ncbi.nlm.nih.gov/pubmed/14967535.

Carvalho V, Castanheira P, Faria T Q, Gonçalves C, Madureira P, Faro C, Domingues L, Brito R M, Vilanova M G M. Biological activity of heterologous murine interleukin-10 and preliminary studies on the use of a dextrin nanogel as a delivery system. *Int J Pharm.* 2010; 400(1-2): 234-42.

Ameer, G A, Crumpler, E T and Langer, R. Cell killing potential of a water-soluble radical initiator, International Journal of Cancer, 2001, Volume 93 Issue 6, 875-879.

Cadée J A, van Luyn M J A, Brouwer L A, Planting a J A, van Wachem P B, De Groot C J, et al. In vivo biocompatibility of dextran-based hydrogels. Inc J Biomed Mater Res. 2000; 50:397-404

Fuertges, F., & Abuchowski, A. The clinical efficacy of poly (ethylene glycol)-modified proteins. *J. Controlled Release,* 1990; 11, 139-148.

Vasey, P., Twelves, C., Kaye, S., Wilson, P., Morrison, R., Duncan, R., et al. (1999). Phase I clinical and pharmacokinetic study of PKI (HPMA copolymer doxorubicin): first member of a new class of chemotherapeutic agents: drug-polymer conjugates. *Clin. Cancer Res,* 5, 83-94.

Hardwicke, J., Ferguson, E. L., Moseley, R., Stephens, P., Thomas, D. W., Duncan, R., et al. (2008). Journal of Controlled Release. *Journal of Controlled Release,* 130, 275-283.

OrientI, I, Zuccari, G, Carosio, R and Montaldo, P G, Improvement of aqueous solubility of fenretinide and other hydrophobic anti-tumor drugs by complexation with amphiphilic dextrins, *Drug Delivery,* 2009; 16(7): 389-398

The following claims set out a particular embodiment of the invention.

The invention claimed is:

1. A hydrogel formulation comprising a hydrogel of oxidized dextrin reticulated with adipic acid dihydrazide comprising the following structure:

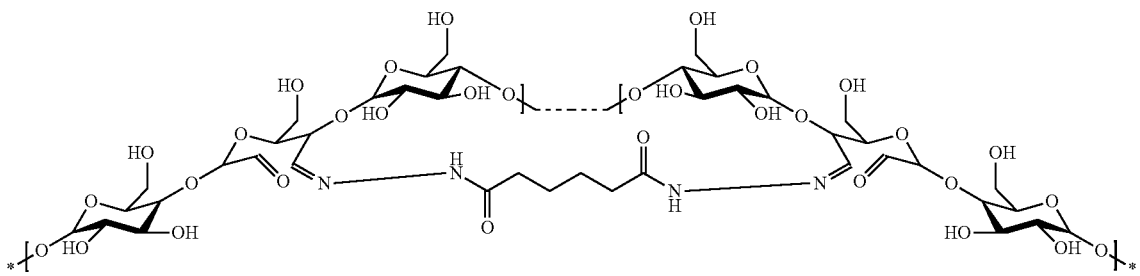

wherein the hydrogel comprises a three-dimensional porous structure, and wherein the three-dimensional porous structure is capable of enclosing polysaccharides, proteins, nanogels, nanoparticles, granular materials, bioactive molecules and/or cells, and wherein the dextrin has a molecular weight between 1200 and 8000 Da.

2. The hydrogel formulation according to claim 1, wherein the proteins comprise collagen, fibronectin, and casein.

3. The hydrogel formulation according to claim 1, wherein the hydrogel formulation comprises proteins, and wherein the proteins are included in a percentage between 0-20% of the hydrogel formulation, by dry weight.

4. The hydrogel formulation according to claim 1, wherein the polysaccharides comprise chitosan and hyaluronic acid.

5. The hydrogel formulation according to claim 1, wherein the hydrogel formulation comprises polysaccharides, and wherein the polysaccharides are included in a percentage between 0-20 of the hydrogel formulation, by dry weight.

6. The hydrogel formulation according to claim 1, wherein the hydrogel formulation is injectable.

7. The hydrogel formulation according to claim 1, wherein the hydrogel formulation is non-toxic.

8. The hydrogel formulation according to claim 1, wherein the hydrogel formulation is non-haemolytic.

9. The hydrogel formulation according to claim 1, wherein the hydrogel is obtained from a dextrin with an oxidation degree between 25-35%.

10. The hydrogel formulation according to claim 1, wherein the hydrogel comprises a continuous porous structure, with a diameter of about 1 μm.

11. The hydrogel formulation according to claim 1, wherein the hydrogel is biodegradable, and wherein biodegradation of the hydrogel occurs by either surface erosion or bulk erosion.

12. The hydrogel formulation according to claim 1, wherein the hydrogel is degradable, and wherein degradation of the hydrogel comprises hydrolytic degradation of covalent intermolecular bonds or enzymatic degradation through action of α-amylase present in human tissues or included in the hydrogel formulation.

13. The hydrogel formulation according to claim 1, wherein the hydrogel is degradable, and wherein degradation occurs by bulk erosion and comprises a non-linear degradation profile accompanied by an increasing pore size.

14. Method of producing the hydrogel formulation of claim 1, comprising:
 a) oxidation of dextrin with periodate;
 b) removal of unreacted periodate;
 c) gelification by addition of adipic acid dihydrazide, at pH in the range 5.0-7.5.

15. The method according to claim 14, wherein the percentage of adipic acid dihydrazide used is between 3-10%, on a molar basis relative to the glucose residues of dextrin.

16. The method according to claim 14, wherein the concentration of oxidized dextrin is between 25-30% (w/v).

17. The method according to claim 14, wherein the gelification occurs during a gelification period of 1 to 30 minutes.

18. The method according to claim 14, wherein a nanogel or nanoparticle is incorporated in the hydrogel.

19. The method according to claim 18 wherein the nanogel or nanoparticle is between 10-10,000 nm in size.

20. The method according to claim 18, wherein incorporation of the nanogel or nanoparticle in the hydrogel is carried out by mixing the nanogel or nanoparticle with the oxidized dextrin, prior to addition of adipic acid dihydrazide.

21. The method according to claim 18, wherein the nanogel or nanoparticle is incorporated in a proportion of 1-25% of the dextrin weight.

22. The method according to claim 18, wherein the nanogel or nanoparticle is previously loaded with pharmaceuticals.

23. A method for tissue regeneration or controlled drug delivery comprising administering the hydrogel of claim 1.

24. A biomaterial comprising the hydrogel described in claim 1.

25. A synthetic bone substitute comprising the hydrogel of claim 1 and obtained by a method comprising:
 a) oxidation of dextrin with periodate;
 b) removal of unreacted periodate;
 c) gelification by addition of adipic acid dihydrazide, at pH in the range 5.0-7.5.

26. A system for controlled drug delivery comprising the hydrogel of claim 1 and obtained by a method comprising:
 a) oxidation of dextrin with periodate;
 b) removal of unreacted periodate;
 c) gelification by addition of adipic acid dihydrazide, at pH in the range 5.0-7.5.

27. A bone implant or bone filler comprising the hydrogel of claim 1 and obtained by a method comprising:
 a) oxidation of dextrin with periodate;
 b) removal of unreacted periodate;
 c) gelification by addition of adipic acid dihydrazide, at pH in the range 5.0-7.5.

28. A composition comprising the hydrogel of claim 1 and obtained by a method comprising:
 a) oxidation of dextrin with periodate;
 b) removal of unreacted periodate;
 c) gelification by addition of adipic acid dihydrazide, at pH in the range 5.0-7.5.

29. A medical prosthesis comprising the hydrogel of claim 1 and obtained by a method comprising:
 a) oxidation of dextrin with periodate;
 b) removal of unreacted periodate;
 c) gelification by addition of adipic acid dihydrazide, at pH in the range 5.0-7.5.

* * * * *